United States Patent
Scaros et al.

(10) Patent No.: US 6,720,446 B2
(45) Date of Patent: Apr. 13, 2004

(54) CATALYST MODIFICATION TO ENHANCE NEOTAME PRODUCTION

(75) Inventors: Mike G. Scaros, Arlington Heights, IL (US); Indra Prakash, Hoffman Estates, IL (US)

(73) Assignee: The NutraSweet Company, Chicago, IL (US)

( * ) Notice: Subject to any disclaimer, the term of this patent is extended or adjusted under 35 U.S.C. 154(b) by 136 days.

(21) Appl. No.: 10/010,381

(22) Filed: Nov. 5, 2001

(65) Prior Publication Data

US 2003/0088119 A1 May 8, 2003

(51) Int. Cl.[7] ............................................ C07C 229/00
(52) U.S. Cl. .......................................... 560/40
(58) Field of Search ..................... 560/40, 41

(56) References Cited

U.S. PATENT DOCUMENTS 5,728,862 A  *  3/1998  Prakash 6,140,538 A  *  10/2000  Rains et al.

OTHER PUBLICATIONS

Cram et al, Journal of the American Chemical Society, Macro Rings. XIII. Synthesis and Properties of 1,7-Cyclododecadiyne and Related Compounds, 1956, 78, pp. 2518–2524.*

Kusaka et al, Applied Catalysis, A: General, Characterization of Unsupported Ru–Co Bimetallic Catalyst Derived from CoCO3, and Its Application for Isophoronenitrile Hydrogenation, 1999, 185(2), pp. 227–235.*

* cited by examiner

Primary Examiner—Johann Richter
Assistant Examiner—Paul A. Zucker
(74) Attorney, Agent, or Firm—Jeffrey M Hoster

(57) ABSTRACT

Processes for using modified catalysts with improved functionality in the production of neotame are disclosed. The modified catalysts surprisingly have been found to improve the selectivity over conventional catalysts and to reduce the level of certain impurities in neotame production processes.

12 Claims, No Drawings

US 6,720,446 B2

CATALYST MODIFICATION TO ENHANCE NEOTAME PRODUCTION

BACKGROUND OF THE INVENTION

1. Field of the Invention

This invention relates to the field of the production of neotame. More particularly, it relates to the field of processes for producing neotame using a catalyst in the reductive alkylation of aspartame with 3,3-dimethylbutyraldehyde to produce neotame.

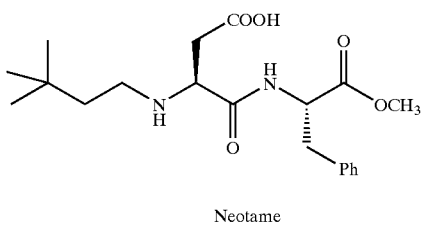

Neotame

2. Description of the Prior Art

The sweetener, N-[N-(3,3-dimethylbutyl)-L-α-aspartyl]-L-phenylalanine 1-methyl ester ("neotame") is a highly intense non-nutritive sweetening agent useful to impart sweetness to a wide variety of food, beverage, and other products. This sweetener was disclosed in U.S. Pat. No. 5,480,668. The sweetener is approximately 8,000 times as sweet as sucrose, with variance depending on level of use and specific product to which it is added.

One production process which has been taught to make neotame is detailed in U.S. Pat. No. 5,510,508. Under this process, reductive alkylation of aspartame with 3,3-dimethylbutyraldehyde takes place. U.S. Pat. No. 5,728,862 teaches further improvements to this type of reductive alkylation. In particular, U.S. Pat. No. 5,728,862 teaches the reductive alkylation of aspartame with 3,3-dimethylbutyraldehyde in methanol. The patent recommends use of hydrogenation catalysts based on platinum or palladium, for example, platinum on activated carbon, palladium on activated carbon, platinum black or palladium black. The patent details a number of other catalysts which can be used. The patent recommends a weight ratio of catalyst to aspartame of about 0.01:1 to about 0.25:1.

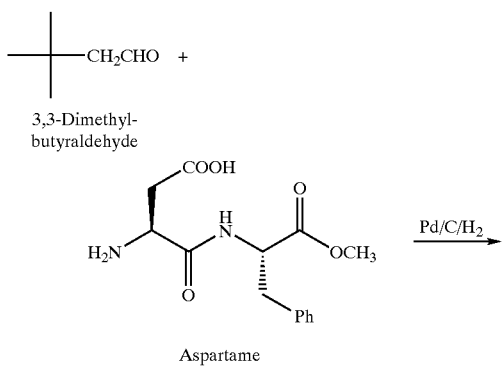

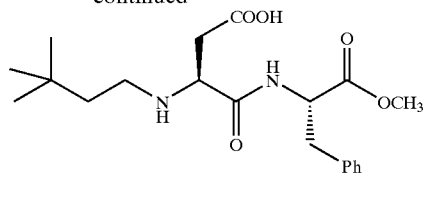

Neotame

There are a number of motivations related to making catalyst use more effective. Catalysts are relatively expensive per pound, so low levels of use and successful recycling processes are two important means to reduce costs. Further, proper selection of catalyst can affect the overall purity and yield of the desired product.

Thus, improved catalyst effectiveness would be highly desirable. The present invention details means for providing such an effective catalyst.

SUMMARY OF THE INVENTION

The present invention is directed to the selection of catalysts in a process for manufacturing neotame. A catalyst is initially selected from the group of catalysts conventionally used in hydrogenation processes. The catalyst is then altered by one of the following methods: 1) multiple re-use in the reductive alkylation produces a catalyst which is more selective and results in a decrease of certain impurities. The catalyst on recycle agglomerated at the surface resulting in lower dispersion of palladium; 2) preparing the initial catalyst with same characteristics as found in the re-cycle catalyst (as described in case 1); 3) addition of catalyst modifiers in the preparation of catalyst or addition of the catalyst modifier in the reductive alkylation process; or 4) co-precipitated bi-metallic catalyst in the reductive alkylation process. Advantages of these catalyst will be in higher purity and yield of neotame which will provide significant opportunities for cost reduction.

DETAILED DESCRIPTION OF THE PREFERRED EMBODIMENT

In a first preferred embodiment, a modified catalyst is used in the reductive alkylation process to make neotame using aspartame and 3,3-dimethylbutyraldehyde. This catalyst is preferably a modified palladium on activated carbon catalyst. The use of the modified catalyst has been shown to reduce the level of dialkylated aspartame, one of the impurities resulting from conventional processes for manufacturing neotame.

The modified catalyst can be produced by recycling catalyst resulting in the agglomeration of the catalyst. It can also be produced directly in the catalyst manufacturing process. Any catalyst conventionally used in hydrogenation reactions is suitable for use and modification hereunder.

In a conventional process for manufacturing neotame, such as the process set forth in U.S. Pat. Nos. 5,510,508; 5,728,862 and U.S. patent application Ser. No. 09/572,843 filed on May 18, 2000, which are incorporated herein by reference, a catalyst is used in the reductive alkylation step of aspartame with 3,3-dimethylbutyraldehyde. This reductive alkylation step is conventionally carried out in the presence of methanol or aqueous methanol, and under pressure conditions between 5 psig and 100 psig hydrogen and temperature conditions between 25–60° C. The catalysts used include, but are not limited to palladium (in a preferred form of a 5% palladium on a carbon support), platinum, rhodium, ruthenium, and nickel. The resulting product, neotame, is isolated, and conventionally, the catalyst is recovered and recycled.

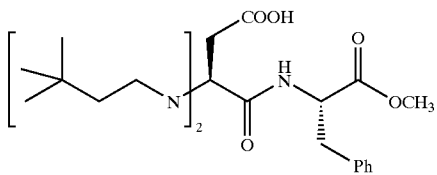

Dialkylated aspartame

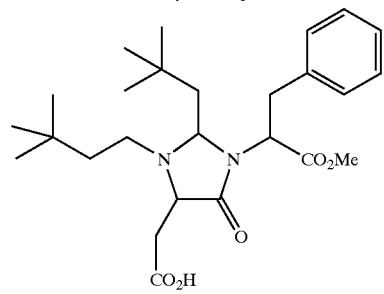

Dialkylated imidazolidinone

Typically, there are small amounts of impurities which are produced during the above process. One of these impurities is dialkylated aspartame [N,N-di (3,3-dimethylbutyl)-L-α-aspartyl-L-phenylalanine 1-methyl ester]. This impurity has been found to be produced in amounts between 1.25–2.50% in conventional neotame coupling processes using fresh palladium catalyst.

When recycled catalyst was used, unexpected low levels of the dialkylated aspartame impurity were produced along with the neotame. In a series of five runs of neotame in which the same catalyst was recycled, the level of the impurity decreased consistently through the five runs. In the first run using fresh catalyst, the level of the dialkylated aspartame impurity was 1.24%. Through the next four runs, the level was 0.98% on the second use of the catalyst, 0.66% on the third use, 0.59% on the fourth use, and 0.56% on the fifth use.

Analysis of the recycled catalyst indicates that the palladium in the fresh catalyst was finely distributed consistently throughout the catalyst. The recycled catalyst showed a different pattern. Overall, the recycled catalyst was found to have less dispersed metal where the palladium agglomerated and moved to the catalyst surface.

Initially modified catalysts, as found in the recycle catalyst, also have been found to improve the overall yield of the process and reduce the level of impurities. Another form of modification is the addition of catalyst modifiers to a catalyst such as 5% palladium on a carbon or other conventional support. The modifiers are preferably selected from the group including, but not limited to, carbon dioxide, quinoline, morpholines, piperizine, pyridine, triphenylphosphine, phosphorous acid, thiocyanates, cyanamid, ethylenediamine, amidines, thiourea, ethyl di-isopropylamine, zinc, lead, silver, copper, mercury, tin, vanadium and other metallic salts, sodium hydroxide, ferrous sulfate or other salts, cadmium sulfate or other salts, and lithium trioxide. The supports are selected from the group comprising carbon, aluminum, silicate, clay, calcium, strontium carbonate, barium sulfate or molecular sieve support.

The palladium catalyst is modified as follows: The catalyst is mixed with the desired modifier either in the preparation of catalyst or addition of the catalyst modifier in the reductive alkylation process. The amount of modifier to be added is selected from ppm-5% level.

The resulting modified catalyst is used in the neotame manufacturing process in the same manner as conventional catalyst, and under the same operating conditions. The catalyst is more selective in forming neotame as opposed to other impurities, therefore, product can be crystallized at higher concentrations, thereby resulting in increased neotame yield.

An additional mechanism for modifying catalysts involves the use of co-precipitated bimetallic metal on carbon or other conventional supports. The preferred bimetallic metal catalyst is a hydrogenation catalyst combined via co-precipitation with a metal from the Group VIII-IIB periodic chart of the elements. Preferred hydrogenation catalysts include, but are not limited to palladium, platinum, rhodium, nickel, and ruthenium. Especially preferred mixtures include 3% palladium/2% rhodium on carbon support and 3% palladium/2% copper on carbon support.

The use of this catalyst in a neotame manufacturing process results in less dialkylated aspartame being produced and an overall greater selectivity. This selectivity is synergistic, as it is considerably greater than what is observed when either of the component metals is used individually with the same total level of use. Further, this allows the subsequent crystallization step to be carried out under conditions in which reduced amounts of methanol and at a higher concentration, which lead to higher yields of neotame.

The co-precipitated catalyst is formed by conventional methods as described in the literature, see Augustine, "Heterogeneous Catalysts for Synthetic Chemist," Marcel Dekker, Inc. 1996 pp268, 301–305.

The modified catalysts above have been proven to reduce impurities and improve yields of neotame in the coupling of 3,3-dimethylbutyraldehyde. It is expected that such catalysts would have similar benefits in the production of neotame by alternative couplings, for example, N-(3,3-dimethylbutyl)-L-aspartic acid. These catalysts will be useful in any such reductive alkylation as long as such reductive alkylations are done in the similar fashion.

The following examples provide further illustration of the inventive concepts herein.

EXAMPLE 1

Aspartame (50.0 g) was charged to a stirred hydrogenation vessel. Then a recycled palladium on carbon catalyst (containing approximately 60% water) was added to the vessel. The loading of the catalyst was 5% on a dry basis at the first use with an additional 0.5% charge of fresh catalyst upon each recycle. This was the fourth recycle of the catalyst. The reactor was pressure purged with nitrogen (4×) and methanol (500 g) was added. The reactor was purged again with nitrogen (4×), then with hydrogen (4×). The vessel was brought up to 40 psi hydrogen and the contents heated to 40° C. Over 4 hours, 16.3 g of 3,3-dimethylbutyraldehyde were pumped into the vessel. The temperature throughout the addition was controlled at 38–40° C. After the aldehyde was added, the line was flushed with methanol (10 ml) to ensure complete charging. When the methanol flush was completed, the reaction solution was stirred under hydrogen pressure for 2 hours. The catalyst was filtered from the methanol solution using powdered cellulose as a filter aid. The catalyst cake was washed with 60 ml of methanol. Analysis of the combined filtrate and wash showed the dialkylated aspartame to neotame ratio to be 0.66%. Methanol was distilled under reduced pressure. The bulk temperature of the solution was kept below 38° C. The solution was concentrated to approximately one-third the original volume. Water and methanol were added to bring the neotame and methanol concentrations to 13% and 27% respectively. The solution was held at 40° C. for 5 hours to hydrolyze the dialkylated imidazolidinone. After testing to ensure the dialkylated imidazolidinone is less than 0.025% (wt), the solution was cooled to 28° C. and seeded with 0.14 g of neotame. The seeded solution was further cooled to 5° C. over 2.5 hours. The filtered solid was washed with 45 ml of cold DI water then dried under house vacuum at 25° C. The yield was 46.03 g (71.6%). The purity of the isolated neotame was >98% and it contained <0.10% of both the dialkylated aspartame and the dialkylated imidazolidinone.

EXAMPLE 2

One hundred grams aspartame was charged to a 1 L stirred vessel. Twenty-six grams of 5% Palladium catalyst on carbon (re-cycled 5 times, about 60% water) was charged to the reactor. 625 g of methanol was added to the reactor. The vessel was purged with nitrogen (4×). While under nitrogen pressure (10 psig) the contents of the vessel were heated to 40° C. Then the vessel was purged with hydrogen (4×) and charged to 40 psig with hydrogen. The agitator was set to 800 rpm. Then 33.2 g of 3,3-dimethylbutyraldehyde was pumped into the vessel over 4–6 hours. The pump and transfer lines were rinsed with 3 ml of methanol (3×) to ensure complete and accurate charging. The mixture was stirred for and additional two hours at 40 psig and 40° C.

After completion of the reductive alkylation, the vessel was vented and purged with nitrogen (4×). The catalyst was removed by filtration through powdered cellulose on a Buchner funnel. The vessel was rinsed with 300 grams of DI water. This rinse was also used to wash the catalyst and combined with the filtrate. An HPLC analysis of the crude reaction mixture indicates 0.56% of dialkylated aspartame.

After addition of the water, the methanol was removed under reduced pressure at or below 40° C. to a methanol content of 25% by weight. The solution was then cooled to 28° C. and seeded with 0.17 g of neotame. The neotame slurry was held at 5° C. for 1 hour. Then the neotame was filtered, and the wet cake was washed with 70 mL cold water. The isolated neotame was dried at 40° C. under vacuum for 48 hours, with 70% yield and neotame purity >98% (by HPLC), dialkylated aspartame (<0.05%) and methylated neotame (<0.05%).

EXAMPLE 3

Aspartame (100 g) was charged into a 1.0 L Parr vessel followed by 3% Palladium/2% Rhodium catalyst on carbon (57.4% wet, 11.7 g) and methanol (319 g). The mixture was stirred for approximately 5 minutes. Water (172 g) was added and the mixture was stirred for approximately 1 minute. The Parr vessel was sealed and purged with nitrogen (3×) followed by hydrogen (3×).

While at 60 psi of hydrogen and a temperature of 40° C., 3-3-dimethylbutyraldehyde (33.2 g) was charged slowly and the reaction mixture was hydrogenated at 40° C. for 13 hours. The catalyst was removed by filtration and washed with deionized water (669 g). The filtrate and washings were combined. The crude hydrogenation mixture contained 89.5% neotame, 7.3% aspartame, 0.6% dialkylated aspartame, and 1.3% dialkylated imidizolidinone.

This crude hydrogenation mixture was placed into a 2-L Erlenmeyer flask. The mixture was hydrolyzed for 3 hours at 40° C. and then cooled to room temperature and seeded at 25° C. The mixture was refrigerated and allowed to statically crystallize overnight. The end temperature of the mixture was 7–8° C. The crystals were filtered, washed with 150 mL cold water and dried under vacuum at 40° C. for 24 hours. The resulting product contained 100% neotame (73% yield based on starting materials). None of the impurities referenced above were detected.

What is claimed is:

1. A process for the reductive alkylation to produce neotame comprising reacting 3,3 dimethylbutyraldehyde and aspartame in the presence of hydrogen, said reductive alkylation carried out by use of one or more hydrogenation catalysts selected from the group consisting of palladium, rhodium, platinum, and ruthenium which (a) have been modified by multiple recycling in a reductive alkylation process, (b) have been modified by the addition of a catalyst modifier to the catalyst or to the reaction mixture in a reductive alkylation process, or (c) have been modified to produce a bi-metallic catalyst by co-precipitation with a metal selected from the group consisting of platinum, palladium, rhodium, ruthenium, copper, iron and tin.

2. The process of claim 1 wherein said hydrogenation catalyst is on a carbon, aluminum, silicate, clay, calcium, strontium carbonate, barium sulfate or molecular sieve support.

3. The process of claim 1 wherein said catalyst modifier is selected from the group consisting of carbon dioxide, quinoline, morpholines, piperizine, pyridine, triphenylphosphine, phosphorous acid, thiocyanates, cyanamid, ethylenediamine, amidines, thiourea, ethyl di-isopropylamine, zinc, lead, silver, copper, mercury, tin, vanadium and other metallic salts, sodium hydroxide, ferrous sulfate or other salts, cadmium sulfate or other salts, and lithium trioxide.

4. The process of claim 1 wherein the ratio of said catalyst to said catalyst modifier is 0.01:1 to 0.25:1.

5. The process of claim 1 wherein the ratio of said catalyst to said metal is 1:1 to 1:0.05.

6. The process of claim 1 wherein said catalyst is agglomerated so that the particle size, amount of palladium on the surface of said catalyst, surface analysis and activity are substantially similar to that of catalyst which has been modified by multiple recycling in an alkylation process.

7. A process for the coupling of 3,3-dimethylbutyraldehyde and aspartame to produce neotame comprising reductive alkylation of said 3,3-dimethylbutyraldehyde and said aspartame in the presence of hydrogen and one or more catalysts selected from the group consisting of palladium, platinum, rhodium, and ruthenium hydrogenation catalysts which (a) have been modified by multiple recycle in a reductive alkylation process, (b) have been modified by the addition of a catalyst modifier to the catalyst or to the reaction mixture in a reductive alkylation process, or (c) have been modified to produce a bi-metallic catalyst by co-precipitation with a metal selected from the group consisting of platinum, palladium, rhodium, ruthenium, copper, iron, and tin.

8. The process of claim 7 wherein said neotame is crystallized in the presence of methanol in an amount of from between 15 and 35% by weight based on neotame.

9. In a process for producing neotame via a hydrogenation reaction whereby said hydrogenation occurs in a reductive alkylation process whereby aspartame and 3,3-dimethylbutyraldehyde are reacted in the presence of hydrogen, the improvement which comprises carrying out said hydrogenation reaction in the presence of a catalyst selected from the group consisting of palladium, platinum, rhodium, and ruthenium hydrogenation catalysts which (a) have been modified by multiple recycle in a reductive alkylation process, (b) have been modified by the addition of a catalyst modifier to the catalyst or to the reaction mixture in a reductive alkylation process, or (c) have been modified to produce a bi-metallic catalyst by co-precipitation with a metal selected from the group consisting of platinum, palladium, rhodium, ruthenium, copper, iron and tin.

10. The process of claim 8 wherein said catalyst is used in an amount of from about 0.01 to about 0.25% based on neotame.

11. The process of claim 10 wherein said catalyst is on a carbon support, said catalyst present in a percentage by weight of 1–10%.

12. A process for improving the selectivity of a hydrogenation catalyst such that said catalyst is capable of reducing dialkylated aspartame impurity to less than 1.0% by weight in a hydrogenation reaction for the production of neotame, comprising the step of modifying said catalyst by the addition of between 5–50% based on the weight of said catalyst of platinum, rhodium, ruthenium, copper, iron or tin to said catalyst.

* * * * *